US00PP08163P

United States Patent [19]

Hoy

[11] Patent Number: Plant 8,163

[45] Date of Patent: Mar. 2, 1993

[54] HYBRID TEA ROSE PLANT NAMED JHILMAR

[75] Inventor: Lowell L. Hoy, Richmond, Ind.

[73] Assignee: Joseph H. Hill Company, Richmond, Ind.

[21] Appl. No.: 724,596

[22] Filed: Jul. 1, 1991

[51] Int. Cl.[5] ..... A01H 5/00

[52] U.S. Cl. ..... Plt./11

[58] Field of Search ..... Plt. 11, 16, 17, 18

[56] References Cited

U.S. PATENT DOCUMENTS

P.P. 3,857 4/1976 Meilland et al. ..... Plt. 18

*Primary Examiner*—Howard J. Locker

*Attorney, Agent, or Firm*—Christie, Parker & Hale

[57] ABSTRACT

A new hybrid tea rose plant producing flowers having a general light pink tonality which develops from orange-hued buds.

1 Drawing Sheet

SUMMARY OF THE INVENTION

The present invention relates to a new and distinct variety of rose plant of the hybrid tea rose class which was originated by my crossing as seed parent the variety known as "Golden Fantasie" (U.S. Plant Pat. No. 3272) and as pollen parent an unnamed and unpatented seedling of my creation. The varietal denomination of this new rose is "JHilmar".

Among the novel characteristics possessed by this new variety which distinguishes it from its parents and all other varieties of which I am aware are flower buds and blooms of unusual coloration which are attractive in fully open and partially open stages borne on a vigorous free branching plant. Flowers open well and remain attractive as blooms age. The new variety is also characterized by its health, vigor and flower production.

Asexual reproduction by budding of the new variety as performed in Richmond, Ind. shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

"JHilmar" is an unusually fine hybrid tea rose of light pink flower coloration. It is especially well suited for growing commercially in greenhouses for cut flower production. The variety blooms freely under greenhouse growing conditions. Greenhouse production of "JHilmar" is greater than its seed parent "Golden Fantasie". The new variety's unique bud and flower color is especially desirable for commercial use.

The following is a detailed description of my new variety, with color terminology in accordance with The Royal Horticultural Society Colour Chart (R.H.S.C.C.). The terminology used in color description herein refers to plate numbers in the aforementioned color chart.

Parentage: Seedling.

*Seed parent.*—"Golden Fantasie".

*Pollen parent.*—Unnamed seedling.

Class: Hybrid tea.

The following information is from observations made of specimens grown in a greenhouse in Richmond, Ind. in the month of Apr.

FLOWER

Blooming habit: Continuous, abundant.

A. Bud:

(1) *Size.*—Medium large.

(2) *Form.*—Long, pointed before calyx breaks; globular as first petals open.

(3) *Color.*—As sepals divide, bud color is near 26C to 26D.

(4) *Sepals.*—Slightly longer than bud; primarily simple; sepals curl back. Color: Inside — near 138C. Outside — near 143C.

(5) *Peduncle.*—Length: Medium. Aspect: Straight, no thorns, prickles or hairs. Strength: Erect, strong. Color: Near 137A.

(6) *Calyx.*—Color: Near 137A; color as calyx breaks — near 26D.

B. Bloom:

(1) *Size.*—Average size when fully expanded — about 3.5 to 4 inches.

(2) *Borne.*—Singly, one to a stem disbudded for commercial production, and in small clusters.

(3) *Form.*—Cupped at first, outer petals quill to points, inner petals roll under.

(4) *Petalage.*—Number of petals under normal conditions — about 35 to 40.

C. Petals:

(1) *Texture.*—Thin, soft.

(2) *Appearance.*—Inside and outside velvety.

(3) *Form.*—Broad, fan shaped, retuse, outer petals have distinct apices after quilling, some petals and petaloids notched.

(4) *Coloration (flower from rose grown in a greenhouse in Apr.).*—Outside petals: Upper surface — near 155D shaded with near 62D at petal margins and washing slightly into the petal from the petal edge; near 10C at point of petal attachment. Under surface — similar to petal top surface but with less near 62D coloration. Inner petals: Upper surface — near 159B to 155D shaded with near 62D at petal margin; near 10C at point of petal attachment but extending further into petal base than in outer petals. Petals approaching flower centers have more prominent yellow coloration and upper surface appears to be mainly yellow tones. Under surface — similar to petal upper surface except that yellow tonality not as pervasive.

(5) *Arrangement.*—Regularly arranged, imbricated.

(6) *Fragrance.*—Moderate.

(7) *Lasting quality.*—Petals persist in greenhouse; cut flowers last 6 days in the month of Apr.

REPRODUCTION ORGANS

A. Stamens:

*Arrangement.*—Irregularly around pistils, tucked in calyx.

*Anthers.*—Size — medium. Color — near 157B with near 168C margin.

*Filaments: (threads).*—Length — medium, most with anthers. Color — near 157D.

*Pollen.*—Color — near 167D, abundant.

B. Pistils:

*Number.*—Many.

*Styles.*—Length — medium, moderately thin, bunched. Color — near 157D at top.

*Stigmas.*—Color — near 161D.

C. Characteristics of ovularies: All encased in calyx.

D. Hips: None observed.

PLANT

A. Form: Upright.

B. Growth: Vigorous, upright; free branching.

C. Foliage: Compound 3 and 5 leaflets.

(1) *Size.*—Medium.

(2) *Quantity.*—Moderately abundant.

(3) *Color.*—Mature upper side — near 136B. Mature under side — near 139C. Young upper side — near 139A. Young under side — near 137B shaded with near 58A.

(4) *Shape.*—Ovoid, acuminate; acute base.

(5) *Texture.*—Leathery; upper side is semi-glossy, under side is matte.

(6) *Edge.*—Serrate.

(7) *Serration.*—Regular.

(8) *Leaf stem.*—Color — near 136A.

(9) *Stipules.*—Medium, narrow with long points at angle less than 45° toward stem.

(10) *Petiolule.*—Small.

(11) *Rachis.*—Upper side — grooved. Under side — sparsely thorny.

D. Wood (1) *New wood.*—Color — near 137B, shaded with near 58A.

(2) *Old wood.*—Color — near 136A.

E. Thorns:

*Quantity (main stalk).*—Average.

*On laterals from stalk.*—Average.

*Form.*—Hooked downward.

*Length.*—Medium.

*Color.*—Near 58A.

*Position.*—Irregular.

*Prickles.*—Few, near 58A in color.

I claim:

1. A new and distinct variety of rose plant of the hybrid tea rose class, substantially as shown and described.

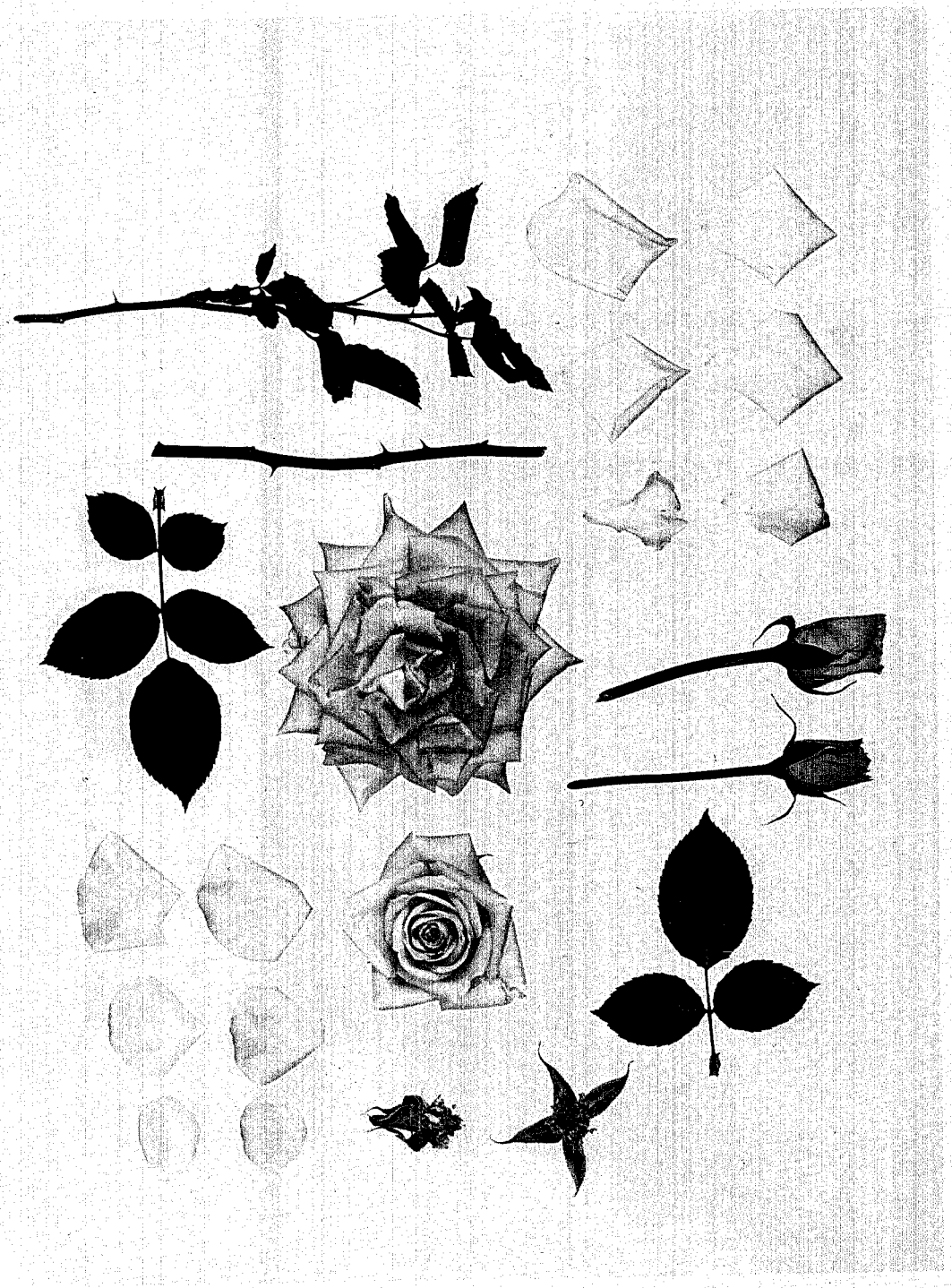

* * * * *